United States Patent [19]
Bremer et al.

[11] Patent Number: 6,143,199
[45] Date of Patent: *Nov. 7, 2000

[54] FLUORINATED BIPHENYLCYCLOHEXANES, AND LIQUID-CRYSTALLINE MEDIUM

[75] Inventors: Matthias Bremer, Darmstadt; Kazuaki Tarumi, Seeheim-Jugenheim; Joachim Krause, Dieburg, all of Germany

[73] Assignee: Merck Patent Gesellschaft mit beschrankter Haftung, Germany

[*] Notice: This patent is subject to a terminal disclaimer.

[21] Appl. No.: 09/093,037

[22] Filed: Jun. 8, 1998

Related U.S. Application Data

[62] Division of application No. 08/639,975, Apr. 29, 1996, Pat. No. 5,807,500.

[30] Foreign Application Priority Data

Apr. 27, 1995 [DE] Germany .......... 195 15 504

[51] Int. Cl.⁷ .......... C09K 19/30; C09K 19/52
[52] U.S. Cl. .......... 252/299.63; 252/299.66
[58] Field of Search .......... 252/299.63, 299.66

[56] References Cited

U.S. PATENT DOCUMENTS

| | | | |
|---|---|---|---|
| 5,122,295 | 6/1992 | Weber et al. | 252/299.01 |
| 5,213,710 | 5/1993 | Reiffenrath et al. | 252/299.63 |
| 5,382,379 | 1/1995 | Onji et al. | 252/299.63 |
| 5,458,805 | 10/1995 | Wachtler et al. | 252/299.63 |
| 5,520,846 | 5/1996 | Plach et al. | 252/299.63 |
| 5,746,941 | 5/1998 | Rieger et al. | 252/299.63 |
| 5,807,500 | 9/1998 | Bremer et al. | 252/299.66 |
| 5,837,162 | 11/1998 | Reiffenrath et al. | 252/299.63 |

FOREIGN PATENT DOCUMENTS

| | | |
|---|---|---|
| 390395 | 10/1990 | European Pat. Off. . |
| 93/02152 | 2/1993 | WIPO . |

OTHER PUBLICATIONS

Abstract of WO 91/08184 (1991).

*Primary Examiner*—C. H. Kelly
*Attorney, Agent, or Firm*—Millen, White, Zelano & Branigan, P.C.

[57] ABSTRACT

Fluorinated biphenylcyclohexanes of the formula I

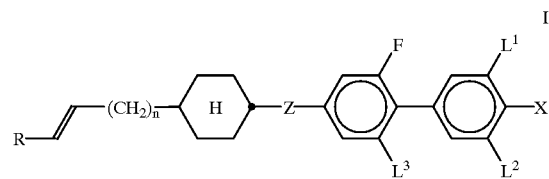

in which

R, X, Z, $L^1$, $L^2$, $L^3$ and n are as defined herein, are suitable as components of liquid-crystalline media.

13 Claims, No Drawings

FLUORINATED BIPHENYLCYCLOHEXANES, AND LIQUID-CRYSTALLINE MEDIUM

This is a divisional of application Ser. No. 08/639,975 filed Apr. 29, 1996, U.S. Pat. No. 5,807,500.

The invention relates to fluorinated biphenylcyclohexanes of the formula I

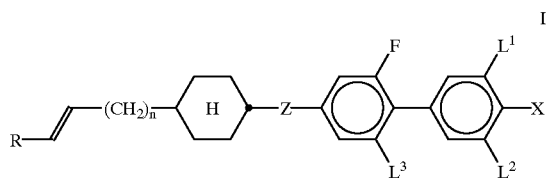

in which
R is H or an alkyl, oxaalkyl or oxaalkenyl radical having 1–6 carbons atoms, the alkyl optionally having a —$CH_2$— group replaced by —CH=CH—,
X is F, Cl, CN or an alkyl, alkoxy, alkenyloxy or alkenyl radical having 1 to 6 carbon atoms which is substituted by one or more fluorine atoms, e.g., up to perhalo substituted,
$L^1$, $L^2$ and $L^3$ are each, independently of one another, H or F,
Z is —$CH_2CH_2$—, —CH=CH—, —C≡C— or a single bond, and
n is 0, 1, 2 or 3,
with the proviso that, in the case where
$L^3$=H, X≠F, Cl, CN, $CF_3$, $OCF_3$ or $OCHF_2$.

The invention furthermore relates to the use of these compounds as components of liquid-crystalline media, and to liquid-crystal and electro-optical display elements which contain the novel liquid-crystalline media.

The compounds of the formula I can be used as components of liquid-crystalline media, in particular for displays based on the principle of the twisted cell, the guest-host effect, the effect of deformation of aligned phases or the effect of dynamic scattering.

BACKGROUND OF THE INVENTION

Similar compounds are described in WO 91/02709 and WO 91/08184. However, the novel compounds are not mentioned therein.

The substances employed hitherto for this purpose all have certain disadvantages, for example excessively high melting points, excessively low clearing points, inadequate stability to the presence of heat, light or electric fields, inadequate electrical resistance, an excessively high temperature dependence of the threshold voltage, or unfavorable dielectric and/or elastic properties.

SUMMARY OF THE INVENTION

An object of the invention was finding novel stable liquid-crystalline or mesogenic compounds which are suitable as components of liquid-crystalline media and in particular simultaneously as comparatively low viscosity and relatively high dielectric anisotropy.

Upon further study of the specification and appended claims, further objects and advantages of this invention will become apparent to those skilled in the art.

It has now been found that compounds of the formula I are eminently suitable as components of liquid-crystalline media. In particular, they have comparatively low viscosities, broad nematic phase ranges and comparatively high clearing points. They can be used to obtain stable-liquid-crystalline media having a broad mesophase range and advantageous optical and dielectric anisotropy values. These media furthermore have very good low-temperature behavior.

In view of the wide variety of areas of application of such compounds of high Δε, however, it was desirable to have available further compounds of high nematogeneity which have properties precisely customized to the particular applications.

In addition, the provision of compounds of the formula I very generally considerably broadens the range of liquid-crystalline substances which are suitable, from various applicational points of view, for the preparation of liquid-crystalline mixtures.

The compounds of the formula I have a broad range of applications. Depending on the choice of substituents, these compounds can be used as base materials from which liquid-crystalline media are predominantly composed; however, compounds of the formula I can also be added to liquid-crystalline base materials from other classes of compounds in order, for example, to affect the dielectric and/or optical anisotropy of a dielectric of this type and/or to optimize its threshold voltage and/or its viscosity.

In the pure state, the compounds of the formula I are colorless and form liquid-crystalline mesophases in a temperature range which is favorably located for electrooptical use. They are stable chemically, thermally and to light.

The invention thus relates to the compounds of the formula I and to the use of these compounds as components of liquid-crystalline media. The invention furthermore relates to liquid-crystalline media comprising at least one compound of the formula I, and to liquid-crystal display elements, in particular electro-optical display elements, which contain such media.

Preference is given to compounds of the formula I in which $L^1$ and/or $L^2$ are fluorine.

X is preferably F, Cl, CN, $OCF_3$, $CF_3$, $CHF_2$, $OCHF_2$, $OCHFCF_3$, $OCH_2CHF_2$, $OCH_2CF_3$, $OCF_2CHF_2$, $OC_2F_5$, $OC_3F_7$, $OCH_2C_2F_5$, OCH=$CF_2$, OCF=$CF_2$, OCF=CF—$CF_3$, OCH=CF—$CF_3$, CH=$CF_2$, $CH_2CF_3$ or $OCHFCHF_2$, in particular F, $OCF_3$, $OCHF_2$, $OCH_2CF_3$, $OCH_2CHF_2$, CN and OCH=$CF_2$. The radical X preferably contains not more than 3 carbon atoms. n is preferably 0 or 1. R is preferably H or methyl.

The alkyl radical R may be straight-chain or branched. It is preferably straight-chain, has 1, 2, 3, 4, 5 or 6 carbon atoms and accordingly is preferably ethyl, propyl, further butyl, pentyl or hexyl.

Oxaalkyl, i.e., alkyl having an oxa atom interrupting the chain, is preferably straight-chain 2-oxapropyl (=methoxymethyl), 2- (=ethoxymethyl) or 3-oxabutyl (=2-methoxyethyl), 2-, 3- or 4-oxapentyl, 2-, 3-, 4- or 5-oxahexyl, or 2-, 3-, 4-, 5- or 6-oxaheptyl.

If R is an alkyl radical in which one $CH_2$ group has been replaced by —CH=CH—, this can be straight-chain or branched. It is preferably straight-chain and has 2 to 7 carbon atoms. Accordingly, it is in particular vinyl, prop-1- or -2-enyl, but-1-, -2- or -3-enyl, pent-I-, -2-, -3- or -4-enyl, hex-1-, -2-, -3-, -4- or -5-enyl, or hept-1-, -2-, -3-, -4-, -5- or -6-enyl.

Of these compounds of the formula I and of the subformulae below, preference is given to those in which at least one of the radicals present therein has one of the preferred meanings indicated.

In the compounds of the formula I, preference is given to the stereoisomers in which the cyclohexylene ring is trans-1,4-disubstituted.

Preferred subgeneric groups of compounds are those of the subformulae I1 to I6:

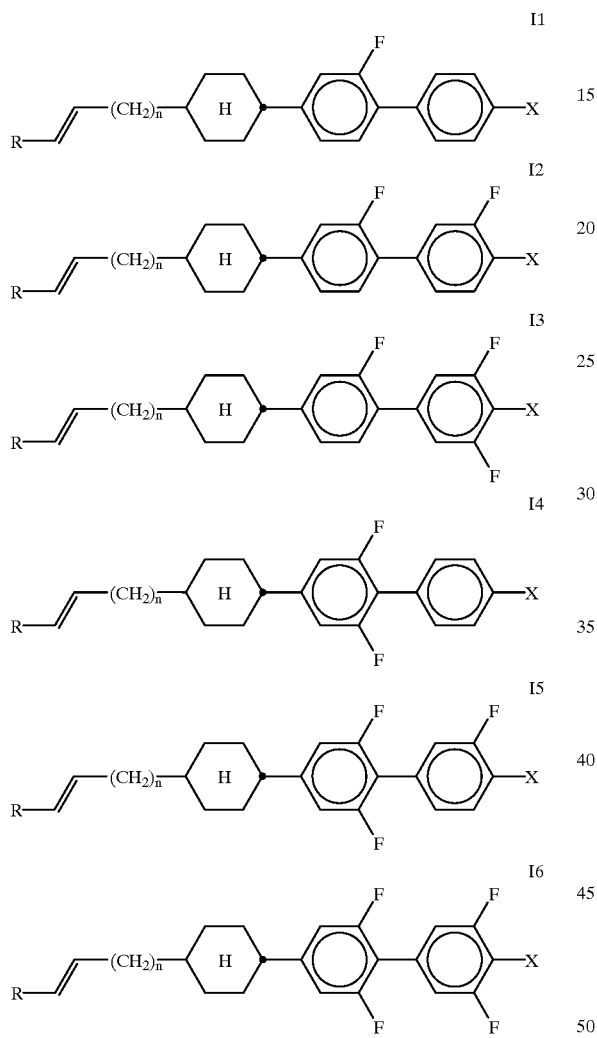

The compounds of the formula I are prepared by methods known per se, as described in the literature (for example in the standard works, such as Houben-Weyl, Methoden der Organischen Chemie [Methods of Organic Chemistry], Georg-Thieme-Verlag, Stuttgart), to be precise under reaction conditions which are known and suitable for said reactions.

Use can also be made of variants which are known per se, but are not mentioned here in greater detail.

For example, the compounds may be prepared according to one of the following reaction schemes:

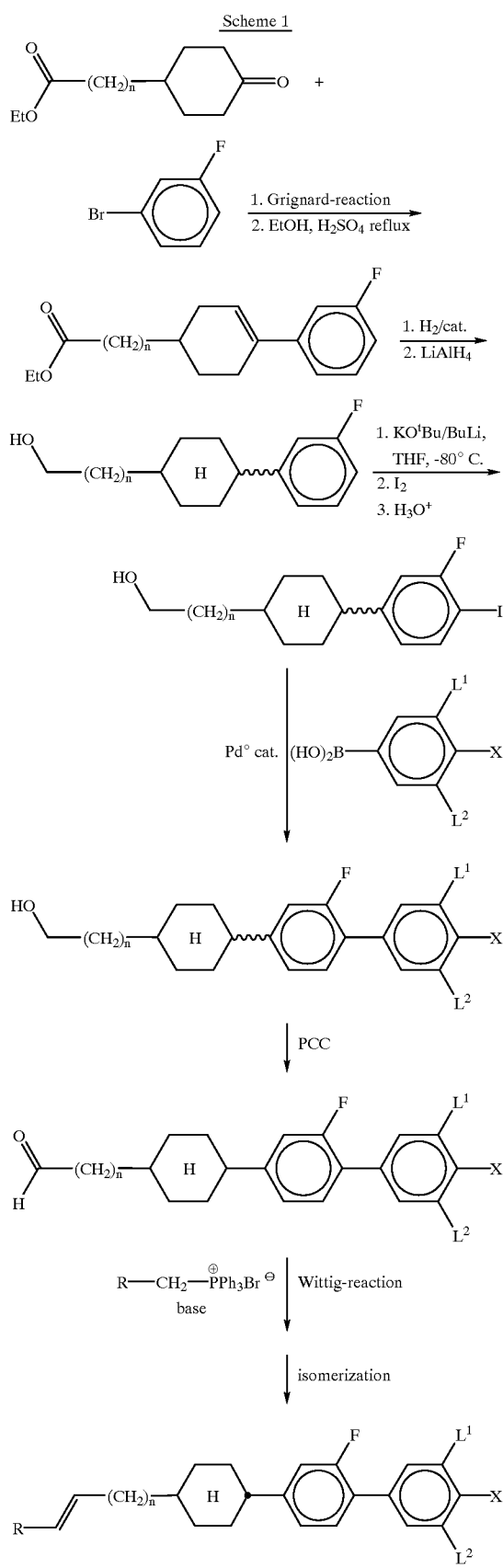

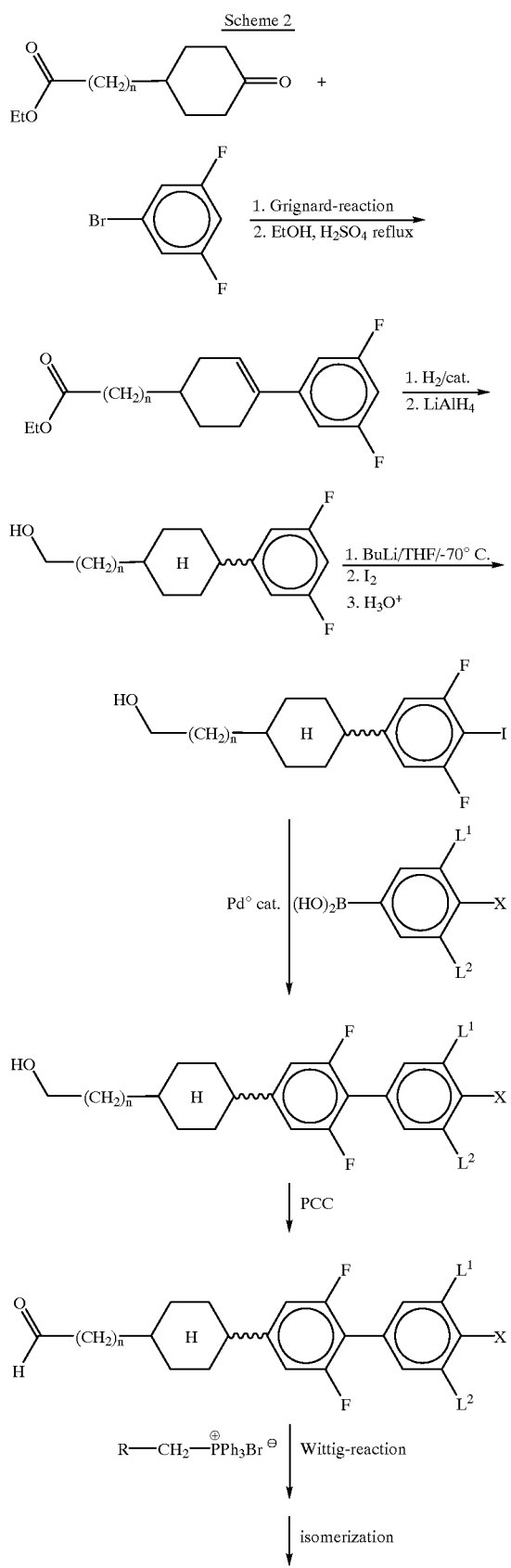

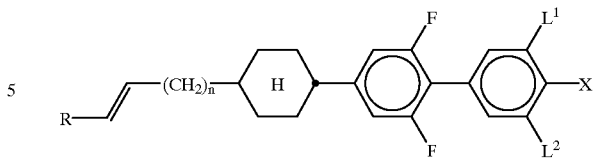

The novel liquid-crystalline media preferably contain 2 to 40, in particular 4 to 30, components as further constituents besides one or more novel compounds. These media very particularly preferably contain 7 to 25 components besides the one or more novel compounds. These further constituents are preferably selected from nematic or nematogenic (monotropic or isotropic) substances, in particular substances from the classes of the azoxy-benzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)-ethanes, 1-cyclohexyl-2-biphenylylethanes, 1-phenyl-2-cyclohexylphenylethanes optionally halogenated stilbenes, benzyl phenyl ethers, tolans and substituted cinnamic acids. The 1,4-phenylene groups in these compounds may also be fluorinated.

The most important compounds suitable as further constituents of novel media can be characterized by the formulae 1, 2, 3, 4 and 5:

| | |
|---|---|
| R'-L-E-R" | 1 |
| R'-L-COO-E-R" | 2 |
| R'-L-OOC-E-R" | 3 |
| R'-L-CH$_2$CH$_2$-E-R" | 4 |
| R'-L-C≡C-E-R" | 5 |

In the formulae 1, 2, 3, 4 and 5, L and E, which may be identical or different, are in each case, independently of one another, a bivalent radical from the group formed by —Phe—, —Cyc—, —Phe—Phe—, —Phe—Cyc—, —Cyc—Cyc—, —Pyr—, —Dio—, —G—Phe— and —G—Cyc— and their mirror images, where Phe is unsubstituted or fluorine-substituted 1,4-phenylene, Cyc is trans-1,4-cyclohexylene or 1,4-cyclohexylene, Pyr is pyrimidine-2,5-diyl or pyridine-2,5-diyl, Dio is 1,3-dioxane-2,5-diyl and G is 2-(trans-1,4-cyclohexyl).ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The novel media preferably comprise one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group ill consisting of —Phe—Phe—, —Phe—Cyc—, —Cyc—Cyc—, —G—Phe— and —G—Cyc—, and optionally one or more components selected from the compounds of the formulae 1, 2, 3, 4 and 5 in which the radicals L and E are selected from the group consisting of —Phe—Cyc—, —Cyc—Cyc—, —G—Phe— and —G—Cyc—.

In a smaller subgroup of the compounds of the formulae 1, 2, 3, 4 and 5, R' and R" are in each case, independently of one another, alkyl, alkenyl, alkoxy, alkoxyalkyl, alkenyloxy or alkanoyloxy having up to 8 carbon atoms. This smaller subgroup is called group A below, and the compounds are labelled with the subformulae 1a, 2a, 3a, 4a and 5a. In most of these compounds, R' and R" are different from one another, one of these radicals usually being alkyl, alkenyl, alkoxy or alkoxyalkyl.

In another smaller subgroup of the compounds of the formulae 1, 2, 3, 4 and 5 which is known as group B, R" is —F, —Cl, —NCS or —(O)$_i$CH$_{3-(k+1)}$F$_k$Cl$_1$, where i is 0 or 1, and k+1 is 1, 2 or 3; the compounds in which R" has this meaning are labelled with the siubformulae 1b, 2b, 3b, 4b and 5b. Particular preference is given to those compounds of the subformulae 1b, 2b, 3b, 4b and 5b in which R" is —F, —Cl, —NCS, —CF$_3$, —OCHF$_2$ or —OCF$_3$.

In the compounds of the subformulae 1b, 2b, 3b, 4b and 5b, R' is as defined for the compounds of the subformulae 1a–5a and is preferably alkyl, alkenyl, alkoxy or alkoxyalkyl.

In a further smaller subgroup of the compounds of the formulae 1, 2, 3, 4 and 5, R" is —CN; this subgroup is known as group C below, and the compounds of this subgroup are correspondingly described by subformulae 1c, 2c, 3c, 4c and 5c. In the compounds of the subformulae 1c, 2c, 3c, 4c and 5c, R' is as defined for the compounds of the subformulae 1a–5a and is preferably alkyl, alkoxy or alkenyl.

In addition to the preferred compounds of groups A, B and C, other compounds of the formulae 1, 2, 3, 4 and 5 having other variants of the proposed substituents are also customary. All these substances can be obtained by methods which are known from the literature or analogously thereto.

Besides novel compounds of the formula I, the novel media preferably comprise one or more compounds selected from group A and/or group B and/or group C. The proportions by weight of the compounds from these groups in the novel media are preferably Group A: 0 to 90%, preferably 20 to 90%, in particular 30 to 90%

Group B: 0 to 80%, preferably 10 to 80%, in particular 10 to 65%

Group C: 0 to 80%, preferably 5 to 80%, in particular 5 to 50%, the sum of the proportions by weight of the group A and/or B and/or C compounds present in the particular novel media preferably being 5 to 90% and in particular 10 to 90%.

The novel media preferably comprise 1 to 40%, particularly preferably 5 to 30%, of the compounds of formula I. Further preferred media are those which comprise more than 40%, in particular 45 to 90%, of the compounds of formula I. The media preferably comprise three, four or five compounds of the formula I.

The novel media are preferably based on more than one (preferably two or more) compounds of the formula I, i.e., the proportion of these compounds preferably being ≧25%, particularly preferably ≧40%.

The individual compounds of the formula I to XII and of their subformulae which can be sued in the novel media are either known or can be prepared analogously to known compounds.

Preferred embodiments are indicated below:

The medium additionally comprises one or more compounds selected from the group consisting of the general formula II, III and IV:

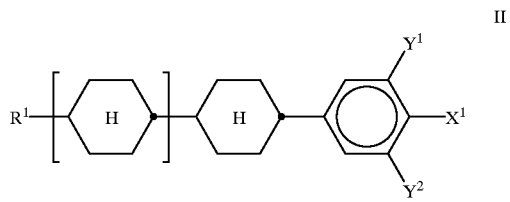

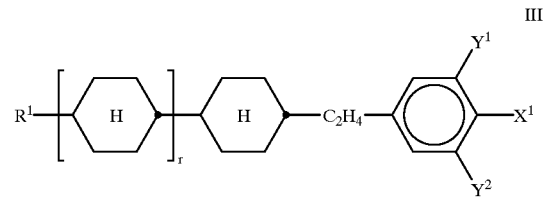

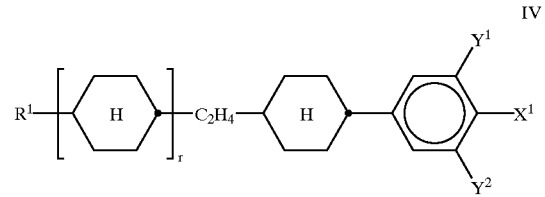

in which the individual radicals have the following meanings:

R$^1$: alkyl, oxaalkyl, fluoroalkyl or alkenyl, in each case having 1 to 7 carbon atoms X$^1$: F, Cl, CF$_3$, OCF$_3$ or OCHF$_2$ Y$^1$ and Y$^2$ each, independently of the other, H or F r: 0 or 1.

The medium additionally comprises one or more compounds selected from the group consisting of the general formulae V to VIII:

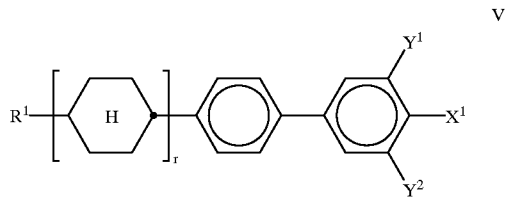

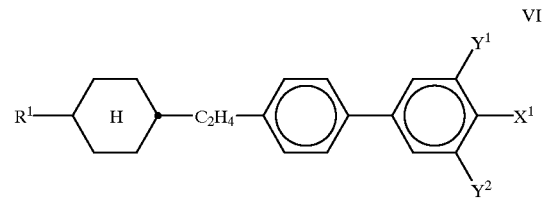

-continued

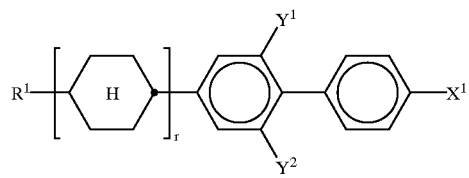
VII

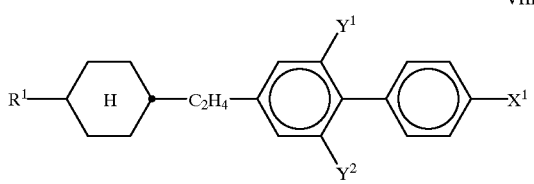
VIII in which $R^1$, $X^1$, $Y^1$ and $Y^2$ each, independently of the others, is as defined above.

The medium additionally comprises one or more compounds selected from the group consisting of the general formulae IX to XII:

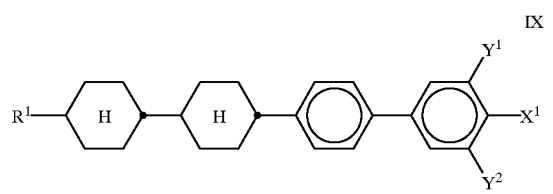
IX

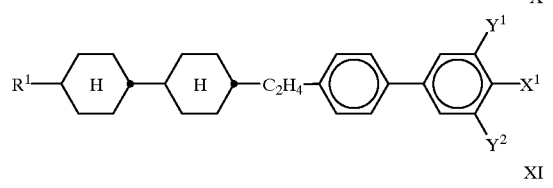
X

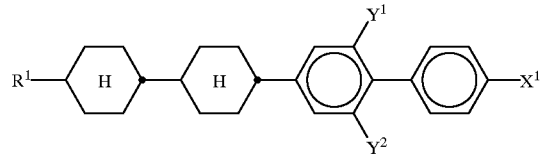
XI

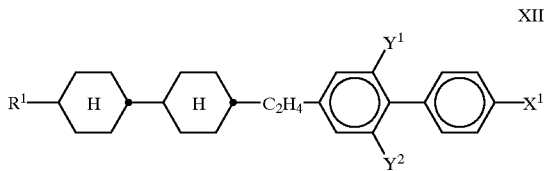
XII in which $R^1$, $X^1$, $Y^1$ and $Y^2$ each, independently of the others, is as defined above.

The proportion of compounds of the formulae I to IV together in the mixture as a whole is at least 50% by weight.

The proportion of compounds of the formula I in the mixture as a whole is from 10 to 50% by weight.

The proportion of compounds of the formulae II to IV in the mixture as a whole is from 30 to 70% by weight.

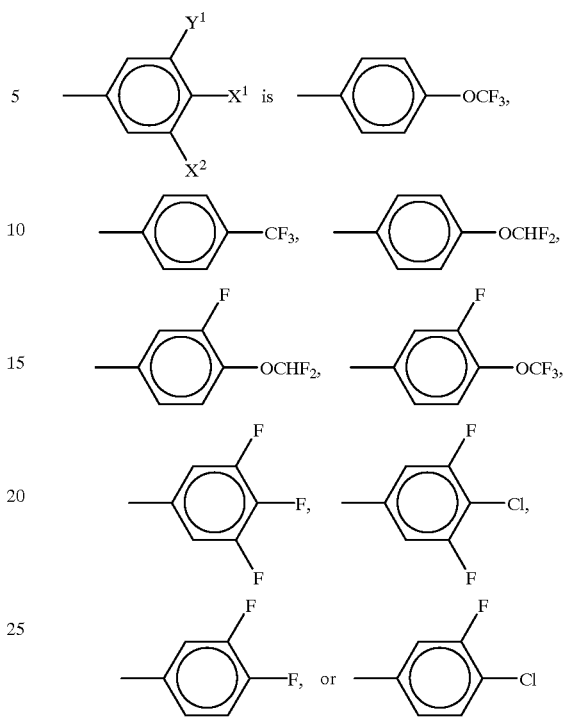

The medium comprises compounds of the formulae II and III or IV.

$R^1$ is straight-chain alkyl or alkenyl having 2 to 7 carbon atoms.

The medium consists essentially of compounds of the formula I to IV.

The medium comprises further compounds, preferably selected from the following group ($Y^1$, $Y^2$ and $Y^3$=H or F):

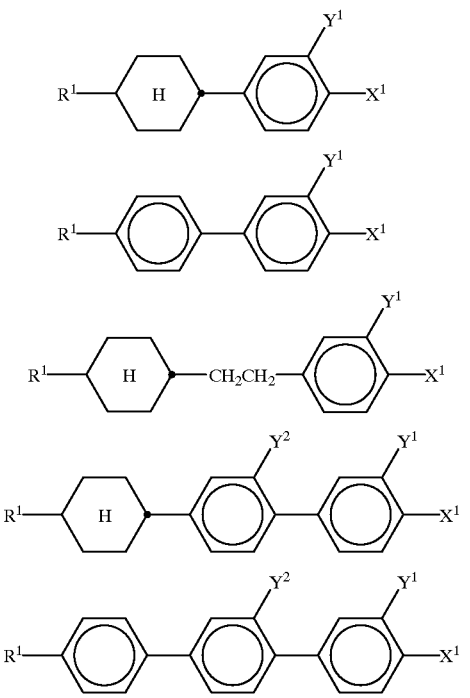

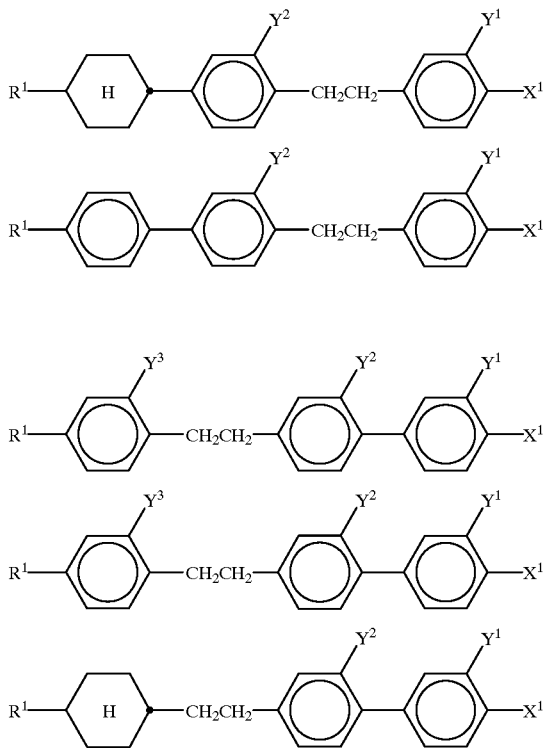

The I: (II+III+IV) weight ratio is preferably from 1:4 to 1:1.

The medium consists essentially of compounds selected from the group consisting of the general formulae I to XII.

It has been found that even a relatively small proportion of compounds of the formula I mixed with conventional liquid-crystal materials, but in particular with one or more compounds of the formulae II, III and/or IV, results in a significant improvement in the response times and in low threshold voltages, and at the same time broad nematic phases with low smectic-nematic transition temperatures are observed. The compounds of the formulae I to IV are colorless, stable and readily miscible with one another and with other liquid-crystal materials.

The "alkyl", as used above, covers straight-chain and branched alkyl groups having 1–7 carbon atoms, in particular the straight-chain groups methyl, ethyl, propyl, pentyl, hexyl and heptyl. Groups having 2–5 carbon atoms are generally preferred.

The term "alkenyl" covers straight-chain and branched alkenyl groups having 2–7 carbon atoms, in particular straight-chain groups. Particular alkenyl groups are $C_2$–$C_7$-1 E-alkenyl, $C_4$–$C_7$-3 E-alkenyl, $C_5$–$C_7$-4-alkenyl, $C_6$–$C_7$-5-alkenyl and $C_7$-6-alkenyl, in particular $C_2$–$C_7$-1 E-alkenyl, $C_4$–$C_7$-3 E-alkenyl and $C_5$–$C_7$-4-alkenyl. Examples of preferred alkenyl groups are vinyl, 1 E-propenyl, 1 E-butenyl, 1 E-pentenyl, 1 E-hexenyl, 1 E-heptenyl, 3-butenyl, 3 E-pentenyl, 3 E-hexenyl, 3 E-heptenyl, 4-pentenyl, 4 Z-hexenyl, 4 E-hexenyl, 4 Z-heptenyl, 5-hexenyl, 6-heptenyl and the like. Groups having up to 5 carbon atoms are generally preferred.

The term "fluoroalkyl" preferably covers straight-chain groups containing terminal fluorine, i.e. fluoromethyl, 2-fluoroethyl, 3-fluoropropyl, 4-fluorobutyl, 5-fluoropentyl, 6-fluorohexyl and 7-fluoroheptyl. However, other positions of fluorine are not excluded.

The term "oxaalkyl" preferably covers straight-chain radicals of the formula $C_nH_{2n+1}$—O—$(CH_2)_m$, in which n and m are each, independently of one another, from 1 to 6. n is preferably 1 and m is preferably from 1 to 6.

A suitable choice of the meanings of R, X and Y allows the response times, the threshold voltage, the steepness of the transmission characteristic lines, etc., to be modified as desired. For example, 1 E-alkenyl radicals, 3 E-alkenyl radicals, 2 E-alkenyloxy radicals and the like generally result in shorter response times, improved nematic tendencies and a higher ratio between the elastic constants $k_{33}$ (bend) and $k_{11}$ (splay) compared with alkyl and alkoxy radicals. 4-Alkenyl radicals, 3-alkenyl radicals and the like generally give lower threshold voltages and smaller values of $k_{33}/k_{11}$ compared with alkyl and alkoxy radicals.

A —$CH_2CH_2$— group in $Z^1$ and/or $Z^2$ generally results in higher values of $k_{33}/k_{11}$ compared with a single covalent bond. Higher values of $k_{33}/k_{11}$ enable, for example, flatter transmission characteristic lines in TN cells with a 90° twist (in order to achieve grey shades) and steeper transmission characteristic lines in STN, SBE and OMI cells (higher multiplexibility), and vice versa.

The optimum mixing ratio of the compounds of the formulae I and II+III+IV depends substantially on the desired properties, on the choice of the components of the formulae I, II, III and/or IV and on the choice of any other components present. Suitable mixing ratios within the abovementioned range can easily be determined from case to case.

The total amount of compounds of the formulae I to XII in the novel mixtures is not crucial. The mixtures can therefore contain one or more further components in order to optimize various properties. However, the observed effect on the response times and the threshold voltage is generally greater the higher the total concentration of compounds of the formulae I to XII.

In a particularly preferred embodiment, the novel media comprise compounds of the formulae II, III, V and/or VII (preferably II and/or III) in which $X^1$ is $CF_3$, $OCF_3$, $OCHF_2$ or F.

The novel media are prepared in a manner which is customary per se. In general, the components are dissolved in one another, expediently at elevated temperature. By means of suitable additives, the liquid-crystal-line phases can be modified in accordance with the invention in a manner such that they can be used in all types of liquid-crystal display elements which have hitherto been disclosed. Additives of this type are known to those skilled in the art and are described in detail in the literature (H. Relker/R. Hatz, Handbook of Liquid Crystals, Verlag Chemie, Weinheim, 1980). For example, pleochroic dyes can be added for the production of coloured guest-host systems, or substances can be added to modify the dielectric anisotropy, the viscosity and/or the orientation of the nematic phases.

In the present application and in the examples below, the structures of the liquid-crystal compounds are indicated by acronyms, the transformation into chemical formulae taking place as in Tables A and B below. All the radicals $C_nH_{2n+1}$ and $C_mH_{2m+1}$ are straight-chain alkyl radicals containing n or m carbon atoms respectively. The coding in Table B is self-evident. In Table A, only the acronym for the parent structure is given. In individual cases, the acronym for the parent structure is followed, separated by a hyphen, from a code for the substituents $R^1$, $R^2$, $L^1$ and $L^2$:

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nF.F.F | $C_nH_{2n+1}$ | F | F | F |
| nCF$_3$ | $C_nH_{2n+1}$ | $CF_3$ | H | H |
| nOCF$_3$ | $C_nH_{2n+1}$ | $OCF_3$ | H | H |
| nOCF$_2$ | $C_nH_{2n+1}$ | $OCHF_2$ | H | H |
| nS | $C_nH_{2n+11}$ | NCS | H | H |
| rVsN | $C_rH_{2r+1}-CH=CH-C_sH_{2s}-$ | CN | H | H |
| rEsN | $C_rH_{2r+1}-O-C_sH_{2s}-$ | CN | H | H |
| nAm | $C_nH_{2n+1}$ | $COOC_mH_{2m+1}$ | H | H |

Preferred mixtures contain compounds from Tables A and B in addition to one or more compounds of the formula I.

TABLE A

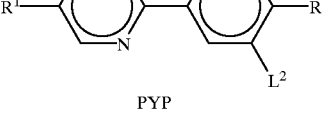

PYP

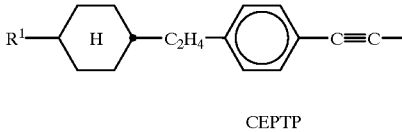

PYRP

BCH

CBC

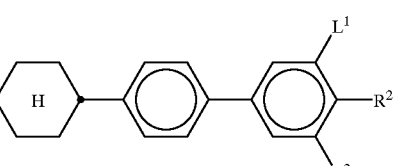

CCH

TABLE A-continued

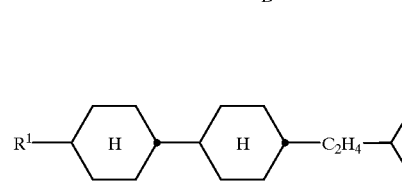

CCP

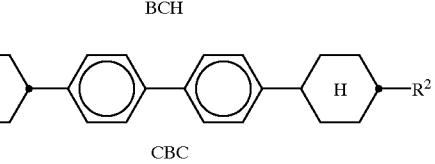

CP

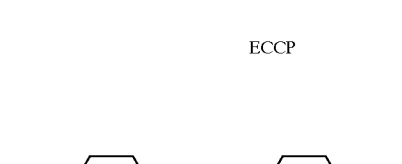

CPTP

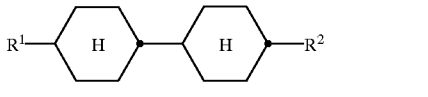

CEPTP

D

ECCP

CECP

TABLE A-continued
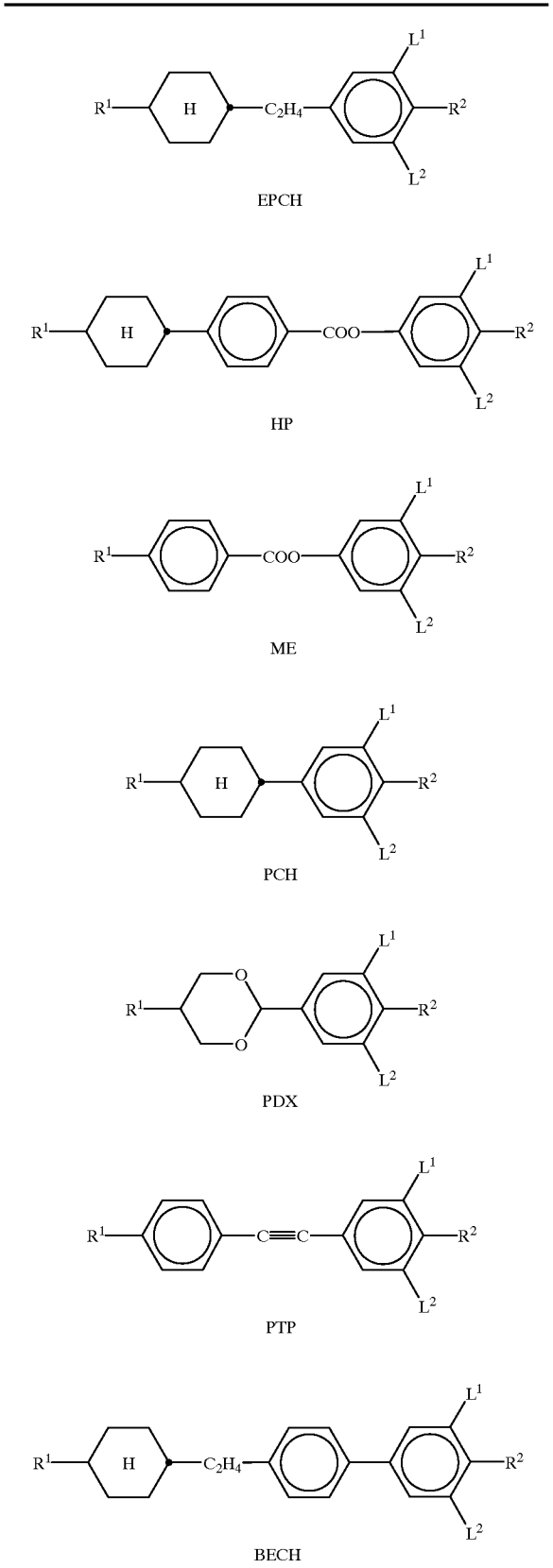
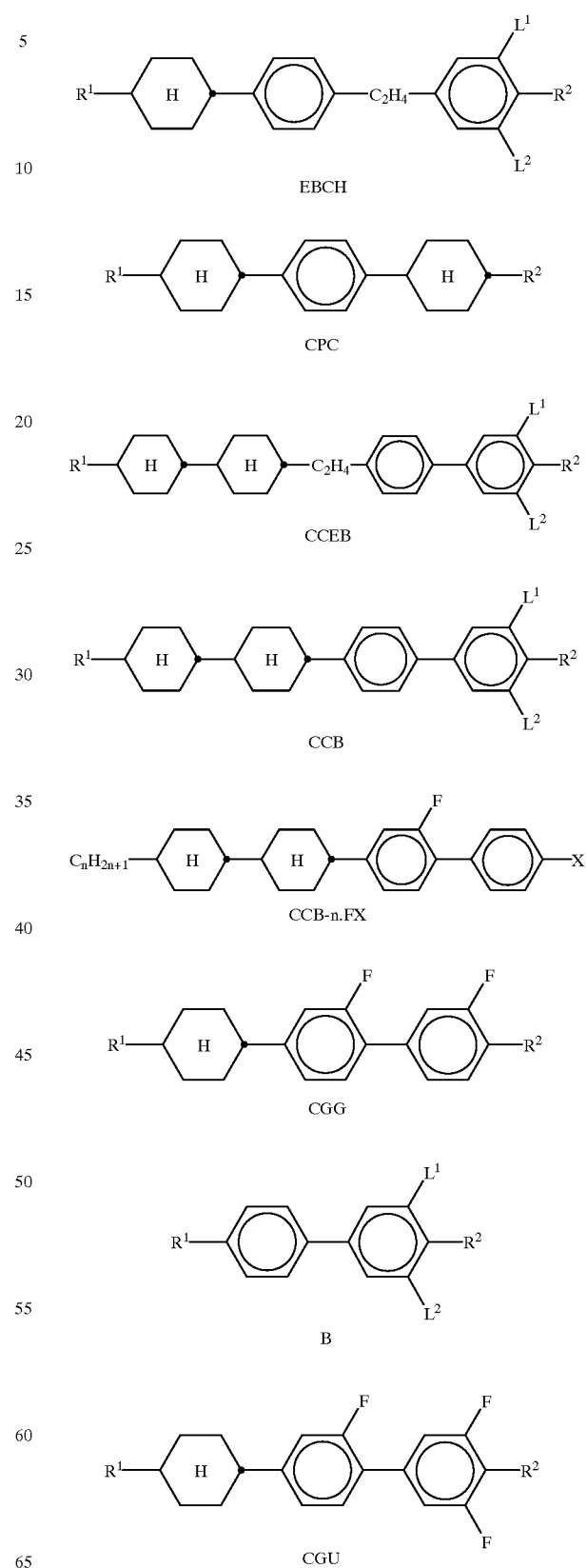

TABLE A-continued
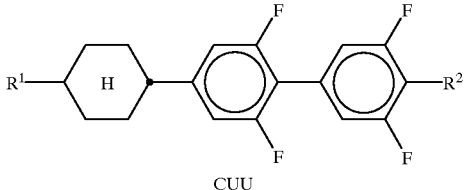
CUU
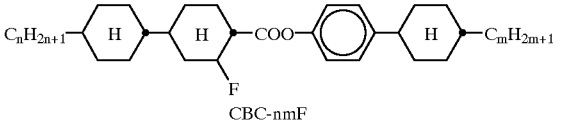
CGG
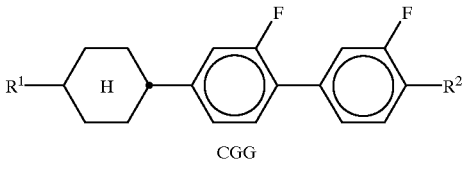
CUG
TABLE B
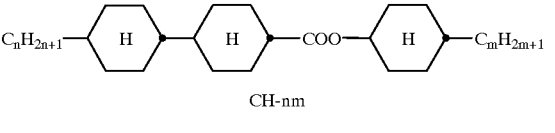
T15
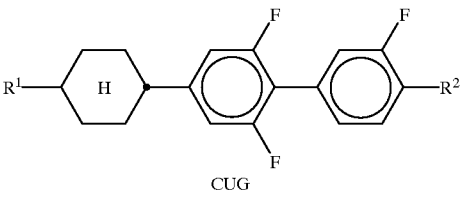
K3n
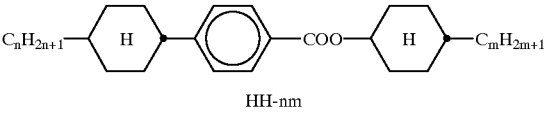
M3n
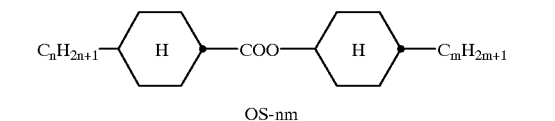
BCH-n.FX
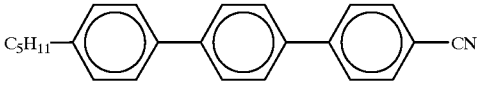
Inm
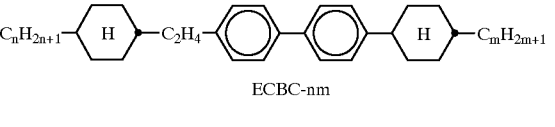
CBC-nmF
TABLE B-continued
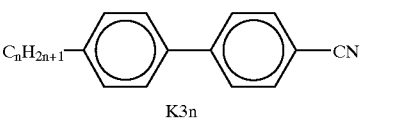
CBC-nmF
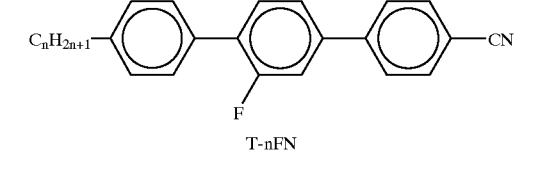
CH-nm
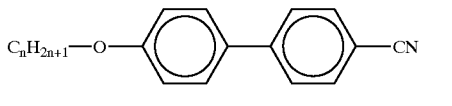
HH-nm
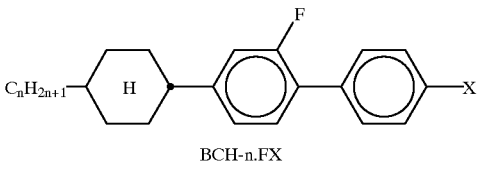
OS-nm
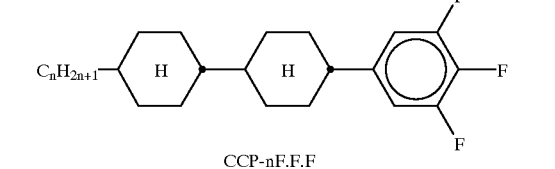
ECBC-nm
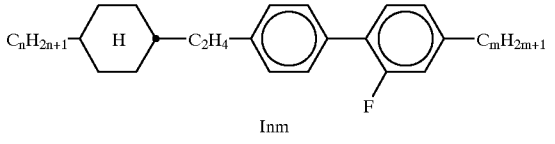
T-nFN
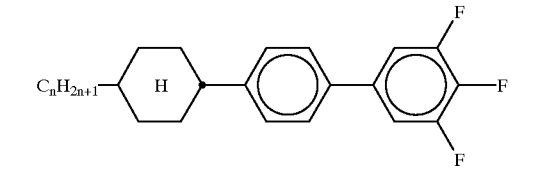
CCP-nF.F.F
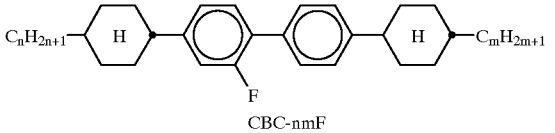
BCH-nF.F.F
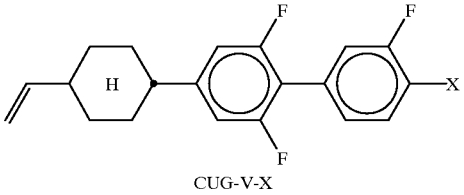
CUG-V-X

TABLE B-continued

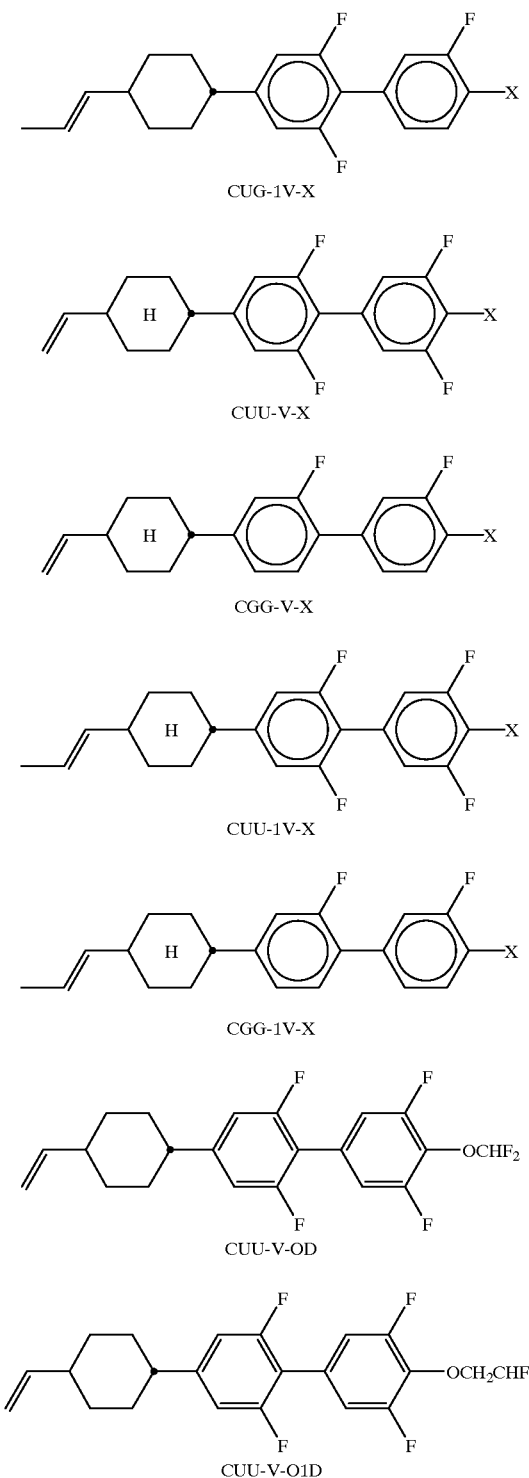

CUG-1V-X

CUU-V-X

CGG-V-X

CUU-1V-X

CGG-1V-X

CUU-V-OD

CUU-V-O1D

The examples below are intended to illustrate the invention without representing a limitation. Above and below, percentages are by weight. All temperatures are given in degrees Celsius. mp. denotes melting point, cp.=clearing point. Furthermore, C=crystalline state, N=nematic phase, S=smectic phase and I=isotropic phase. The data between these symbols represent the transition temperatures. Δn denotes optical anisotropy (589 nm, 20° C.), and the viscosity (mm²/sec) was determined at 20° C.

"Conventional work-up" means that water is added if appropriate, the mixture is extracted with dichloromethane, diethyl ether, methyl tert-butyl ether or toluene, the organic phase is separated off, dried and evaporated, and the product is purified by distillation under reduced pressure or crystallization and/or chromatography. The following abbreviations are used:

DAST diethylaminosulphur trifluoride
DMEU 1,3-dimethyl-2-imidazolidinone
POT potassium tert-butoxide
THF tetrahydrofuran
pTsOH p-toluenesulphonic acid

EXAMPLE 1

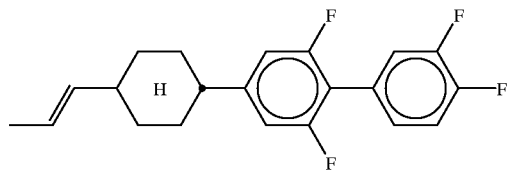

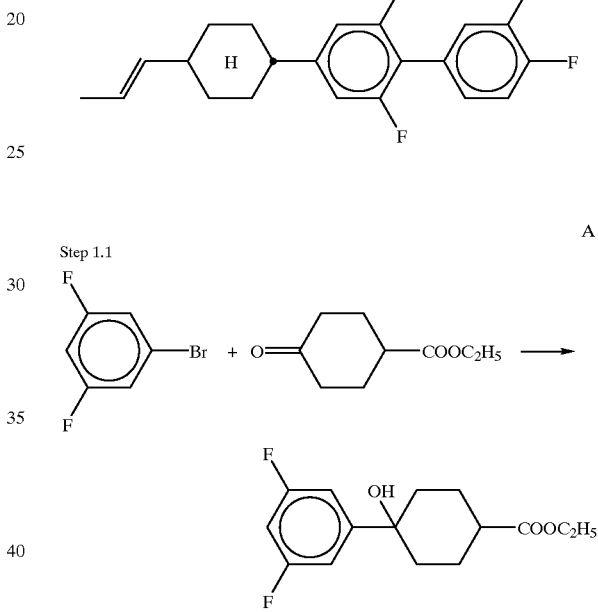

Step 1.1

0.05 mol of 3,5-difluorobenzene in 50 ml of THF is added dropwise under a nitrogen atmosphere to 0.075 mol of magnesium turnings. The mixture is subsequently refluxed for 1 hour and allowed to cool to room temperature. 0.05 mol of methyl 4-cyclohexanone-carboxylate dissolved in 50 ml of THF is subsequently added dropwise to the reaction mixture at such a rate that the internal temperature does not exceed 30° C. The mixture is stirred for 1 hour, hydrolyzed and finally subjected to conventional work-up.

Step 1.2

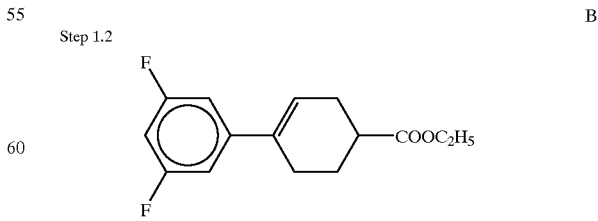

1.4 mol of A are dissolved in 2 l of ethanol and 100 ml of conc. sulphuric acid, and the mixture is refluxed for 4 hours. The vast majority of the ethanol is removed by distillation, and the residue is cooled to room temperature. Water and methyl tert-butyl ether are added, and the product is subjected to conventional work-up.

Step 1.3

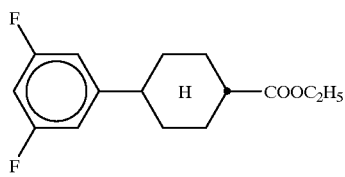

C 1.13 mol of B are dissolved in 2.5 l of THF and hydrogenated at room temperature using 35 g of Pd/c catalyst. When the hydrogenation is complete, the catalyst is filtered off, and the filtrate is subjected to fractional distillation.

b.p.: 90–120° C. ($2\times10^{-5}$ mbar)

Step 1.4

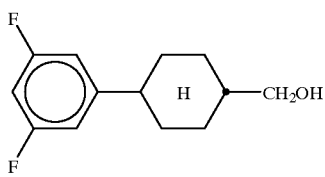

D 0.12 mol of C is dissolved in 100 ml of THF under a nitrogen atmosphere, and 0.12 mol of borane/THF complex (1 molar solution) is added at 0° C. The mixture is stirred at 0° C. for 1 hour, allowed to warm to room temperature and stirred overnight. The reaction mixture is hydrolyzed using $H_2O$/THF (1:1) and subjected to conventional work-up.

Step 1.5

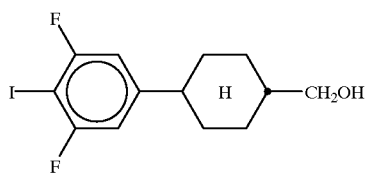

E 88 mmol of D are dissolved in 100 ml of THF under a nitrogen atmosphere, and 0.176 mol of BuLi (1.6 molar solution in n-hexane) is added at −70° C. The mixture is stirred at −70° C. for a further 1 hour, and a solution of 88 mmol of iodine in 100 ml of THP is added dropwise to the reaction mixture at −30° C. When the addition is complete, the mixture is stirred at from −25 to −30° C. for a further hour and then allowed to warm to room temperature. Water, dilute HCl and a sodium hydrogen-sulphite solution are added, and the reaction mixture is finally subjected to conventional work-up.

Step 1.6

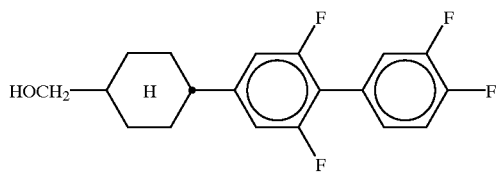

F 0.086 mol of E, 0.086 mol of 3,4-difluorobenzene-boronic acid, 0.170 mol of sodium carbonate in 120 ml of water, 200 ml of ethanol, 120 ml of toluene and 0.5 g of tetrakis (triphenylphosphine) palladium(0) are refluxed for 4 hours. The reaction mixture is allowed to cool to room temperature and then subjected to conventional work-up.

Step 1.7

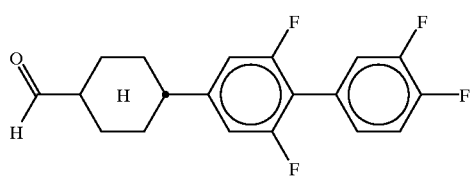

G 78 mmol of F are dissolved in 200 ml of dichloromethane, 99 mmol of pyridinium chlorochromate and 13.7 g of Celite are added at room temperature, and the mixture is stirred overnight. 10 ml of isopropanol are added, the mixture is stirred for 0.5 hour, and the Celite is filtered off with suction. The filtrate is diluted with water and subjected to conventional work-up.

Step 1.8

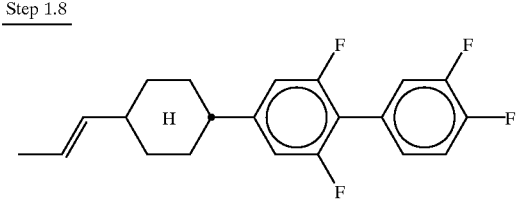

4.3 g of potassium tert-butoxide are added in portions at 15–20° C. to 38.7 mmol of G and 38.7 mmol of ethyltriphenylphosphonium bromide in 100 ml of THF. The mixture is stirred at room temperature for 2 hours, water and dilute HCl are added, and the product is subjected to conventional work-up and recrystallized from ethyl acetate/hexane (1:1).

18.1 mmol of the product, 4.7 mmol of sodium benzenesulphinate, 7.2 mmol of 1 N HCl, 30 ml of toluene and 15 ml of TEF are refluxed for 48 hours in order to effect E/Z isomerization. The reaction mixture is cooled and rendered alkaline by means of 2 molar sodium carbonate solution, and the aqueous phase is separated off and subjected to conventional work-up. The product is recrystallized from ethanol.

C 113 I; $\Delta n=+0.114$; $\Delta\epsilon=12.73$

EXAMPLE 2

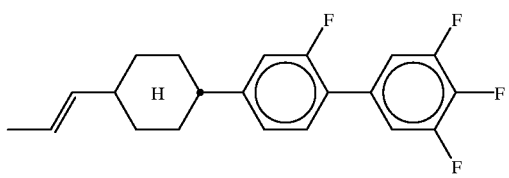

Step 2.1

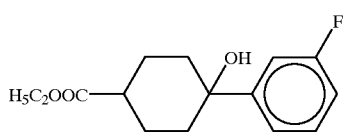

1.1 mol of magnesium turnings in 100 ml of THF are warmed. A solution of 1.1 mol of 1-bromo-3-fluorobenzene and 700 ml of THF is then added dropwise under reflux. The mixture is refluxed for 1 hour and cooled to 10° C., and 1.0 mol of ethyl 4-cyclohexanonecarboxylate in 400 ml of THF is added dropwise to the reaction mixture at 10–20° C. The mixture is stirred at 20° C. for a further 0.5 hour, and 50 ml of water and 200 ml of methyl tert-butyl ether are subsequently added. Finally, the product is subjected to conventional work-up.

Step 2.2

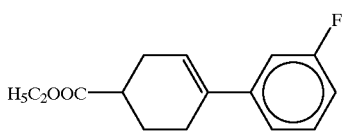

0.75 mol of H, 1125 ml of ethanol and 75 ml of sulphuric acid are refluxed for 4 hours. The reaction mixture is evaporated in a rotary evaporator, and water and methyl tert-butyl ether are added to the residue. Finally, the product is subjected to conventional work-up.

Step 2.3

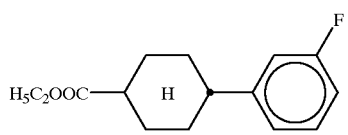

0.74 mol of I is dissolved in 1.8 l of THF, 35 g of Pd/C (5%) are added, and the mixture is hydrogenated. When the hydrogenation is complete, the catalyst is filtered off, and the filtrate is evaporated in a rotary evaporator. The residue is subjected to fractional distillation.

b.p.: 103–113° C./0.3 mbar

Step 2.4

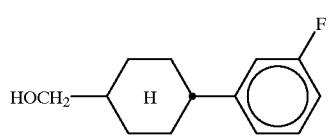

0.82 mol of J is added dropwise at 5–15° C. to 0.82 mol of lithium aluminium hydride in 1.1 l of diethyl ether. When the addition is complete, the mixture is stirred for 0.5 hour and is subsequently hydrolyzed using water and 20% sulphuric acid. The mixture is stirred for a further 0.5 hour and subjected to conventional work-up.

Step 2.5

L

HOCH₂—H—F—I 0.1 mol of K dissolved in 100 ml of THF is added dropwise at −80° C. to 0.2 mol of potassium tert-butoxide in 100 ml of THF. 0.2 mol of butyllithium (15% in n-hexane) is subsequently added dropwise to the reaction mixture at −80° C. The mixture is stirred for a further 0.5 hour and diluted with 100 ml of THF, and 0.1 mol of iodine in 100 ml of THF is added dropwise to the reaction mixture. The mixture is subsequently warmed to room temperature, hydrolyzed and is subjected to conventional work-up.

Step 2.6

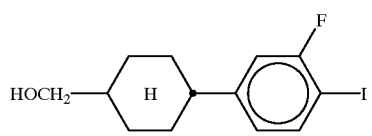

200 ml of toluene and then, one after the other, 0.19 mol of boronic acid in 400 ml of ethanol and 0.38 mol of sodium carbonate in 240 ml of water are added to 0.19 mol of L. Finally, 5.7 mmol of tetrakistriphenyl-phosphinepalladium (O) are added to the reaction mixture. The reaction mixture is refluxed overnight and allowed to cool to room temperature, toluene is added, and the product is subjected to conventional work-up.

Step 2.7

N 0.198 mol of pyridinium chlorochromate and 32 g of Celite are added to 0.19 mol of M in 570 ml of dichloromethane, and the mixture is stirred at room temperature for 18 hours. 30 ml of isopropanol are added, and the mixture is stirred for a further 0.5 hour. The Celite is filtered off with suction and washed with 75 ml of dichloromethane. The filtrate is subjected to conventional work-up.

Step 2.8

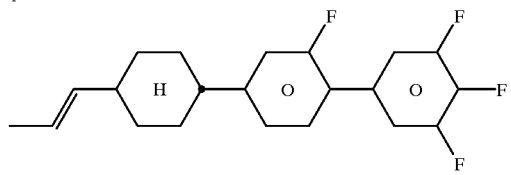

0.1 mol of potassium tert-butoxide is added in portions at 15–20° C. to 0.1 mol of N, 0.1 mol of ethyl-triphenylphosphonium bromide and 240 ml of tetrahydrofuran. The reaction mixture is stirred at room temperature for 2 hours. 100 ml of water are added, the pH is adjusted to 7 using 2 N HCl, and the mixture is subjected to conventional work-up.

The product (42 mmol) is dissolved in 70 ml of toluene and 35 ml of tetrahydrofuran, 10.9 mmol of sodium benzenesulphinate and 16.7 ml of 1 N HCl are added, and the mixture is refluxed for 4 days. After the mixture has been cooled to room temperature, 25 ml of 2 molar sodium carbonate solution are added, and the mixture is subjected to conventional work-up.

The following properties are observed.
C 94 I; $\Delta n=+0.136$; $\Delta\epsilon=15.26$ The following compounds of the formula

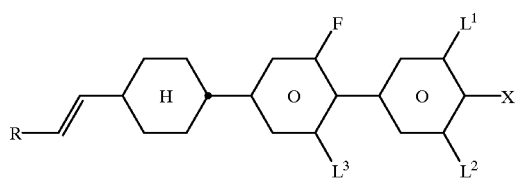

are prepared analogously:

| R | $L^1$ | $L^2$ | $L^3$ | X | |
|---|---|---|---|---|---|
| H | H | H | H | F | |
| H | F | H | H | F | C66N(41.2)I; $\Delta n = +0.132$; $\Delta\epsilon = 7.09$ |
| H | H | H | F | F | |
| H | F | H | F | F | C92 I, $\Delta n = +0.111$; $\Delta\epsilon= 10.64$ |
| H | F | F | F | F | C 139 I |
| H | F | F | H | F | C 82 I, $\Delta n = +0.115$; $\Delta\epsilon = 12.82$ |
| $CH_3$ | H | H | H | F | |
| $CH_3$ | H | H | F | F | |
| $CH_3$ | F | H | H | F | C 67 N 93, 4 I; $\Delta n = +0.155$; $\Delta\epsilon = 10.46$ |
| $CH_3$ | F | F | F | F | C 157 I |
| $C_2H_5$ | H | H | H | F | |
| $C_2H_5$ | H | H | F | F | |
| $C_2H_5$ | F | F | F | F | |
| $C_2H_5$ | F | H | F | F | |
| H | H | H | H | Cl | |
| H | H | H | F | Cl | |
| H | F | F | F | Cl | |
| H | F | H | F | Cl | |
| $CH_3$ | H | H | H | Cl | |
| $CH_3$ | H | H | F | Cl | |
| $CH_3$ | F | F | F | Cl | |
| $C_2H_5$ | H | H | H | Cl | |
| $C_2H_5$ | H | H | F | Cl | |
| $C_2H_5$ | F | F | F | Cl | |
| $C_2H_5$ | F | H | F | Cl | |
| H | H | H | H | CN | |
| H | H | H | F | CN | |
| H | F | F | F | CN | |
| H | F | H | F | CN | |
| $CH_3$ | H | H | H | CN | |
| $CH_3$ | H | H | F | CN | |
| $CH_3$ | F | F | F | CN | |
| $C_2H_5$ | H | H | H | CN | |
| $C_2H_5$ | H | H | F | CN | |
| $C_2H_5$ | F | F | F | CN | |
| $C_2H_5$ | F | H | F | CN | |
| H | H | H | H | $OCF_3$ | |
| H | H | H | F | $OCF_3$ | |
| H | F | F | F | $OCF_3$ | |
| H | F | H | F | $OCF_3$ | |
| H | F | H | H | $OCF_3$ | c 25N 46.3I; $\Delta n = +0.129$; $\Delta\epsilon = 9.89$ |
| $CH_3$ | H | H | H | $OCF_3$ | |
| $CH_3$ | F | H | H | $OCF_3$ | c49N 91.0I; $\Delta n = +0.140$; $\Delta\epsilon = 12.39$ |
| $CH_3$ | H | H | F | $OCF_3$ | |
| $CH_3$ | F | F | F | $OCF_3$ | |
| $C_2H_5$ | H | H | H | $OCF_3$ | |
| $C_2H_5$ | H | H | F | $OCF_3$ | |
| $C_2H_5$ | F | F | F | $OCF_3$ | |
| $C_2H_5$ | F | H | F | $OCF_3$ | |
| H | H | H | H | $CF_3$ | |
| H | H | H | F | $CF_3$ | |
| H | F | F | F | $CF_3$ | |
| H | F | H | F | $CF_3$ | |
| $CH_3$ | H | H | H | $CF_3$ | |
| $CH_3$ | H | H | F | $CF_3$ | |
| $CH_3$ | F | F | F | $CF_3$ | |
| $C_2H_5$ | H | H | H | $CF_3$ | |
| $C_2H_5$ | H | H | F | $CF_3$ | |
| $C_2H_5$ | F | F | F | $CF_3$ | |
| $C_2H_5$ | F | H | F | $CF_3$ | |
| H | H | H | H | $CCHF_2$ | |
| H | H | H | F | $OCHF_2$ | |
| H | F | F | F | $OCHF_2$ | C 66 I; $\Delta n = +0.104$; $\Delta\epsilon = 12.23$ |
| H | F | H | F | $OCHF_2$ | |
| $CH_3$ | H | H | H | $OCHF_2$ | |
| $CH_3$ | H | H | F | $OCHF_2$ | |
| $CH_3$ | F | F | F | $OCHF_2$ | |
| $C_2H_5$ | H | H | H | $OCHF_2$ | |
| $C_2H_5$ | H | H | F | $OCHF_2$ | |
| $C_2H_5$ | F | F | F | $OCHF_2$ | |
| $C_2H_5$ | F | H | F | $OCHF_2$ | |
| H | H | H | H | $OCHFCF_3$ | |
| H | H | H | F | $OCHFCF_3$ | |
| H | F | F | F | $OCHFCF_3$ | |
| H | F | H | F | $OCHFCF_3$ | |
| $CH_3$ | H | H | H | $OCHFCF_3$ | |
| $CH_3$ | H | H | F | $CCHFCF_3$ | |
| $CH_3$ | F | F | F | $OCHFCF_3$ | |
| $C_2H_5$ | H | H | H | $OCHFCF_3$ | |
| $C_2H_5$ | H | H | F | $OCHFCF_3$ | |
| $C_2H_5$ | F | F | F | $OCHFCF_3$ | |
| $C_2H_5$ | F | H | F | $CCHFCF_3$ | |
| H | H | H | H | $OC_2F_5$ | |
| H | H | H | F | $OC_2F_5$ | |
| H | F | F | F | $OC_2F_5$ | |
| H | F | H | F | $OC_2F_5$ | |
| $CH_3$ | H | H | H | $OC_2F_5$ | |
| $CH_3$ | H | H | F | $OC_2F_5$ | |
| $CH_3$ | F | F | F | $OC_2F_5$ | |
| $C_2H_5$ | H | H | H | $OC_2F_5$ | |
| $C_2H_5$ | H | H | F | $OC_2F_5$ | |
| $C_2H_5$ | F | F | F | $OC_2F_5$ | |
| $C_2H_5$ | F | H | F | $OC_2F_5$ | |
| H | H | H | H | $OC_3F_7$ | |
| H | H | H | F | $OC_3F_7$ | |

-continued

| R | L$^1$ | L$^2$ | L$^3$ | X | |
|---|---|---|---|---|---|
| H | F | F | F | OC$_3$F$_7$ | |
| H | F | H | F | OC$_3$F$_7$ | |
| CH$_3$ | H | H | H | OC$_3$F$_7$ | |
| CH$_3$ | H | H | F | OC$_3$F$_7$ | |
| CH$_3$ | F | F | F | OC$_3$F$_7$ | |
| C$_2$H$_5$ | H | H | H | OC$_3$F$_7$ | |
| C$_2$H$_5$ | H | H | F | OC$_3$F$_7$ | |
| C$_2$H$_5$ | F | F | F | OC$_3$F$_7$ | |
| C$_2$H$_5$ | F | H | F | OC$_3$F$_7$ | |
| H | H | H | H | C$_2$F$_5$ | |
| H | H | H | F | C$_2$F$_5$ | |
| H | F | F | F | C$_2$F$_5$ | |
| H | F | H | F | C$_2$F$_5$ | |
| CH$_3$ | H | H | H | C$_2$F$_5$ | |
| CH$_3$ | H | H | F | C$_2$F$_5$ | |
| CH$_3$ | F | F | F | C$_2$F$_5$ | |
| C$_2$H$_5$ | H | H | H | C$_2$F$_5$ | |
| C$_2$H$_5$ | H | H | F | C$_2$F$_5$ | |
| C$_2$H$_5$ | F | F | F | C$_2$F$_5$ | |
| C$_2$H$_5$ | F | H | F | C$_2$F$_5$ | |
| H | H | H | H | OCH$_2$CF$_3$ | |
| H | H | H | F | OCH$_2$CF$_3$ | |
| H | F | F | F | OCH$_2$CF$_3$ | |
| H | F | H | F | OCH$_2$CF$_3$ | |
| CH$_3$ | H | H | H | OCH$_2$CF$_3$ | |
| CH$_3$ | H | H | F | OCH$_2$CF$_3$ | |
| CH$_3$ | F | F | F | OCH$_2$CF$_3$ | |
| C$_2$H$_5$ | H | H | H | OCH$_2$CF$_3$ | |
| C$_2$H$_5$ | H | H | F | OCH$_2$CF$_3$ | |
| C$_2$H$_5$ | F | F | F | OCH$_2$CF$_3$ | |
| C$_2$H$_5$ | F | H | F | OCH$_2$CF$_3$ | |
| H | H | H | H | OCH$_2$CHF$_2$ | |
| H | H | H | F | OCH$_2$CHF$_2$ | |
| H | F | F | F | OCH$_2$CHF$_2$ | C 77 I; Δn = +0.120; Δε = 12.06 |
| H | F | H | F | OCH$_2$CHF$_2$ | |
| CH$_3$ | H | H | H | OCH$_2$CHF$_2$ | |
| CH$_3$ | H | H | F | OCH$_2$CHF$_2$ | |
| CH$_3$ | F | F | F | OCH$_2$CHF$_2$ | |
| C$_2$H$_5$ | H | H | H | OCH$_2$CHF$_2$ | |
| C$_2$H$_5$ | H | H | F | OCH$_2$CHF$_2$ | |
| C$_2$H$_5$ | F | F | F | OCH$_2$CHF$_2$ | |
| C$_2$H$_5$ | F | H | F | OCH$_2$CHF$_2$ | |

MIXTURE EXAMPLES

Example A

| | | |
|---|---|---|
| PCH-5F | 9.50% | Clearing point [° C.]: 90.3 |
| PCH-6F | 7.68% | Δn [589 nm, 20 ° C.]: +0.0981 |
| PCH-7F | 5.70% | Δε [1 kHz, 20° C.]: 6.41 |
| CCP-20CF$_3$ | 7.60% | |
| CCP-30CF$_3$ | 11.48% | |
| CCP-40CF$_3$ | 8.55% | |
| CCP-50CF$_3$ | 8.55% | |
| BCH-3F.F | 11.40% | |
| BCH-5F.F | 9.50% | |
| ECCP-30CF$_3$ | 4.75% | |
| ECCP-50CF$_3$ | 4.75% | |
| CBC-33F | 1.90% | |
| CBC-53F | 1.90% | |
| CBC-55F | 1.90% | |
| CUG-1V-F | 5.00% | |

Example B

| | | |
|---|---|---|
| PCH-5F | 9.0% | Clearing point [° C.]: 84 |
| PCH-6F | 7.2% | Δn [589 nm, 20° C.]: +0.0987 |
| PCH-7F | 5.4% | Δε [1 kHz, 20° C.]: 6.99 |
| CCP-20CF$_3$ | 7.2% | |
| CCP-30CF$_3$ | 10.8% | |
| CCP-40CF$_3$ | 8.1% | |
| CCP-50CF$_3$ | 8.1% | |
| BCH-3F.F | 10.8% | |
| BCH-5F.F | 9.0% | |
| ECCP-30CF$_3$ | 4.5% | |
| ECCP-50CF$_3$ | 4.5% | |
| CBC-33F | 1.8% | |
| CBC-53F | 1.8% | |
| CBC-55F | 1.8% | |
| CUG-V-F | 10.0% | |

Example C

| | | |
|---|---|---|
| PCH-5F | 9.0% | Clearing point [° C.]: 82.6 |
| PCH-6F | 7.2% | Δn [589 nm, 20° C.]: +0.0980 |
| PCH-7F | 5.4% | Δε [1 kHz, 20° C.]: 6.75 |
| CCP-20CF$_3$ | 7.2% | |
| CCP-30CF$_3$ | 10.8% | |
| CCP-40CF$_3$ | 8.1% | |
| CCP-50CF$_3$ | 8.1% | |
| BCH-3F.F | 10.8% | |
| BCH-5F.F | 9.0% | |
| ECCP-30CF$_3$ | 4.5% | |
| ECCP-50CF$_3$ | 4.5% | |
| CBC-33F | 1.8% | |
| CBC-53F | 1.8% | |
| CBC-55F | 1.8% | |
| CUU-V-OD | 10.00% | |

Example D

| | | |
|---|---|---|
| PCH-5F | 9.0% | Clearing point [° C.]: 86.61 |
| PCH-6F | 7.2% | Δn [589 nm, 20° C.]: +0.0996 |
| PCH-7F | 5.4% | Δε [1 kHz, 20° C.]: 6.51 |
| CCP-20CF$_3$ | 7.2% | |
| CCP-30CF$_3$ | 10.8% | |
| CCP-40CF$_3$ | 8.1% | |
| CCP-50CF$_3$ | 8.1% | |
| BCH-3F.F | 10.8% | |
| BCH-5F.F | 9.0% | |
| ECCP-30CF$_3$ | 4.5% | |
| ECCP-50CF$_3$ | 4.5% | |
| CBC-33F | 1.8% | |
| CBC-53F | 1.8% | |
| CBC-55F | 1.8% | |
| CUU-V-O1D | 10.0% | |

Example E

| | | |
|---|---|---|
| PCH-5F | 3.60% | Clearing point [° C.]: 116 |
| CCP-20CF$_2$.F.F | 19.17% | Δε [589 nm, 20° C.]: 9.1 |
| CCP-30CF$_2$.F.F | 18.00% | K$_3$/K$_1$: 1.55 |
| CCP-50CF$_2$.F.F | 19.17% | V$_{(10,0,20)}$ [V]: 1.16 |
| CUP-2F.F | 6.03% | |
| CUP-3F.F | 6.03% | |
| CBC-33F | 6.03% | |
| CBC-53F | 6.03% | |
| CBC-55F | 5.94% | |
| CGU-1V-F | 10.00% | |

Example F

| | | | |
|---|---|---|---|
| PCH-5F | 9.0% | Clearing point [° C.]: | 88.3 |
| PCH-6F | 7.2% | Δn [589 nm, 20° C.]: | 0.1008 |
| PCH-7F | 5.4% | Δε [1 kHz, 20° C.]: | 5.8 |
| CCP-20CF$_3$ | 7.2% | Viscosity [20° C.]: | 15 |
| CCP-30CF$_3$ | 10.8% | | |
| CCP-40CF$_3$ | 8.1% | | |
| CCP-50CF$_3$ | 8.1% | | |
| BCH-3F.F | 10.8% | | |
| BCH-5F.F | 9.0% | | |
| ECCP-30CF$_3$ | 4.5% | | |
| ECCP-50CF$_3$ | 4.5% | | |
| CBC-33F | 1.8% | | |
| CBC-53F | 1.8% | | |
| CBC-55F | 1.8% | | |
| CGG-V-F | 10.0% | | |

What is claimed is:

1. A liquid-crystalline medium comprising one or more compounds of the formula I

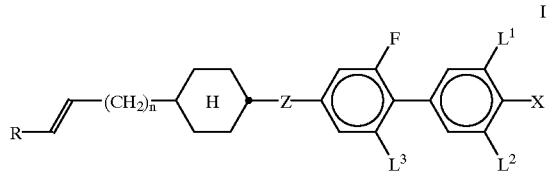

in which

R is H or an alkyl, oxaalkyl or oxaalkenyl radical having 1–6 carbon atoms, alkyl optionally having a —CH$_2$— group replaced by —CH=CH—, X is F, Cl, CN or an alkyl, alkoxy, alkenyloxy or alkenyl radical having 1 to 6 carbon atoms which is substituted by one or more fluorine atoms, L$^1$ is F, L$^2$ is H or F, L$^3$ is H, Z is —CH$_2$CH$_2$—, —CH=CH—, or —C≡C— [or a single bond], and n is 0, 1, 2 or 3.

2. A liquid-crystalline medium according to claim 1, wherein X is F, Cl, CN, CF$_3$, OCHF$_2$, OCF$_3$ or OCHFCF$_3$.

3. A liquid-crystalline medium according to claim 1, further comprising one or more compounds selected from the group consisting of those of the formulae II, III and IV

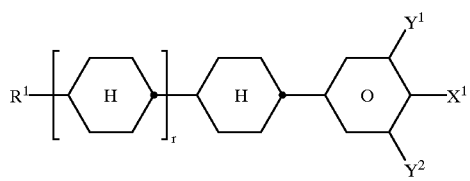

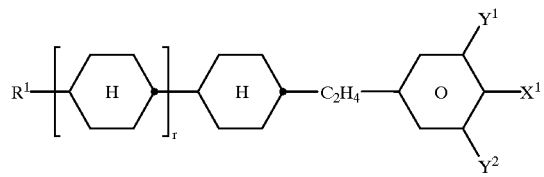

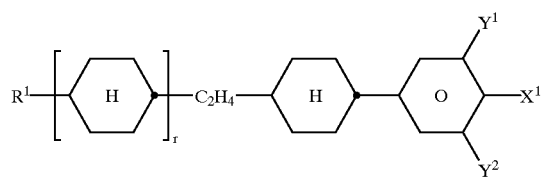

in which

R$^1$ is alkyl, oxaalkyl, fluoroalkyl or alkenyl, each having 1 to 7 carbon atoms, X$^1$ is F, Cl, CF$_3$, OCF$_3$ or OCHF$_2$, Y$^1$ and Y$^2$ are each, independently of the other, H or F, and r is 0 or 1.

4. The medium of claim 1, wherein in formula I, X is a radical containing not more than 3 carbon atoms.

5. The medium of claim 1, wherein in formula I, n is 0 or 1.

6. The medium of claim 1, wherein in formula I, R is H or methyl.

7. The medium of claim 1, wherein the medium comprises 1 to 40% by weight of compounds of the formula I.

8. The medium of claim 1, wherein the medium comprises 5 to 30% by weight of compounds of the formula I.

9. The medium of claim 1, wherein the medium comprises more than 40% by weight of compounds of the formula I.

10. The medium of claim 1, wherein the medium comprises 45 to 90% by weight of compounds of the formula I.

11. The medium of claim 1, wherein the medium comprises three, four or five different compounds of the formula I.

12. The medium of claim 3, wherein the medium comprises at least 50% by weight of compounds of the formulae I to IV.

13. The medium of claim 3, wherein the medium consists essentially of compounds of the formulae I to IV.

* * * * *